United States Patent
Kyung et al.

(10) Patent No.: US 11,502,452 B2
(45) Date of Patent: Nov. 15, 2022

(54) CONNECTOR COVER AND ULTRASONIC PROBE ASSEMBLY HAVING THE SAME

(71) Applicant: SAMSUNG MEDISON CO., LTD., Gangwon-do (KR)

(72) Inventors: Yoonsung Kyung, Seoul (KR); Jin Ho Gu, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 17/151,769

(22) Filed: Jan. 19, 2021

(65) Prior Publication Data
US 2021/0234306 A1    Jul. 29, 2021

(30) Foreign Application Priority Data
Jan. 28, 2020    (KR) .................. 10-2020-0009792

(51) Int. Cl.
*H01R 13/627* (2006.01)
*A61B 8/00* (2006.01)
*H01R 13/52* (2006.01)

(52) U.S. Cl.
CPC ....... *H01R 13/6273* (2013.01); *A61B 8/4455* (2013.01); *H01R 13/5219* (2013.01); *H01R 2201/12* (2013.01)

(58) Field of Classification Search
CPC .............. H01R 13/4532; H01R 13/631; H01R 13/6273; H01R 13/5219; E05F 1/1207; A61B 8/4455
USPC ........................................ 439/135, 901, 892
See application file for complete search history.

(56) References Cited

U.S. PATENT DOCUMENTS

| | | | | |
|---|---|---|---|---|
| 6,685,491 B2* | 2/2004 | Gergek | ............... | H01R 13/005 439/135 |
| 7,059,877 B2* | 6/2006 | Guzelderli | ........... | H01R 13/447 439/142 |
| 7,195,512 B2* | 3/2007 | Jenkinson | .......... | H01R 13/6395 439/372 |
| 7,481,664 B1* | 1/2009 | Knoll | ................. | H01R 13/6275 439/359 |
| 10,149,661 B2 | 12/2018 | Matsummura et al. | | |

(Continued)

FOREIGN PATENT DOCUMENTS

JP    H05-285133 A    11/1993
JP    2003-325529 A    11/2003

(Continued)

OTHER PUBLICATIONS

Extended European Search Report dated Jun. 10, 2021 issued in European Patent Application No. 21152773.4.

*Primary Examiner* — Gary F Paumen
(74) *Attorney, Agent, or Firm* — Morgan, Lewis & Bockius LLP

(57) ABSTRACT

Disclosed herein is a connector cover configured to be used in an ultrasonic probe connector and an ultrasonic probe assembly. The connector cover includes a case, and a coupling device disposed at one end portion in the case and configured to be coupled to the connector. The coupling device includes a body including a fastening portion configured to be coupled to a connector protrusion provided to protrude from the connector toward a first direction, and a rotating shaft connected to the case and the body, and the connector cover is configured to be coupled to the connector along a second direction.

19 Claims, 13 Drawing Sheets

(56) References Cited

U.S. PATENT DOCUMENTS

| | | | |
|---|---|---|---|
| 2003/0100206 A1* | 5/2003 | Rosa | H01R 13/4532 |
| | | | 439/135 |
| 2004/0063348 A1 | 4/2004 | Jenkinson et al. | |
| 2015/0064963 A1* | 3/2015 | Gerullis | H01R 13/5213 |
| | | | 439/521 |
| 2016/0192903 A1 | 7/2016 | Nordgren et al. | |

FOREIGN PATENT DOCUMENTS

| | | |
|---|---|---|
| JP | 2007-195844 A | 8/2007 |
| JP | 2018-175548 A | 11/2018 |
| KR | 10-1406551 B1 | 6/2014 |
| KR | 10-1482996 B1 | 1/2015 |

\* cited by examiner

CONNECTOR COVER AND ULTRASONIC PROBE ASSEMBLY HAVING THE SAME

CROSS-REFERENCE TO RELATED APPLICATION(S)

This application is based on and claims priority under 35 U.S.C. § 119 to Korean Patent Application No. 10-2020-0009792, filed on Jan. 28, 2020 in the Korean Intellectual Property Office, the disclosure of which is incorporated by reference herein in its entirety

BACKGROUND

1. Field

The disclosure relates to an ultrasonic probe assembly, and more particularly, to a cover of an ultrasonic probe connector.

2. Description of Related Art

As there is a growing interest in the importance of sterilization according to the risk of infection in hospitals, the issues relate to the sterilization of medical device emerge. Representative sterilization equipment used for ultrasonic medical devices is a low-temperature plasma sterilizer that converts hydrogen peroxide into plasma and sterilizes the medical devices. After sterilization, hydrogen peroxide is vaporized into water, and thus it has the advantage that it is safe and does not harm the human body. Therefore, the low-temperature plasma sterilizer is widely used for sterilizing an ultrasonic probe. Recently, regulations and laws of the sterilization method for reusable medical devices have expanded, and thus there is a growing need of developing products compatibility with sterilization and disinfection.

If the low-temperature plasma sterilizer is used frequently, the life of the ultrasonic probe may be shortened due to corrosion of the printed circuit board and the connector of the ultrasonic probe exposed to hydrogen peroxide.

SUMMARY

It is an aspect of the disclosure to provide a connector cover and an ultrasonic probe assembly capable of preventing corrosion and damage of a printed circuit board and an ultrasonic probe connector by a sterilizer.

It is another aspect of the disclosure to provide a connector cover and an ultrasonic probe assembly having improved product reliability according to corrosion and damage prevention.

It is another aspect of the disclosure to provide a connector cover capable of being easily coupled to an ultrasonic probe connector.

Additional aspects of the disclosure will be set forth in part in the description which follows and, in part, will be obvious from the description, or may be learned by practice of the disclosure.

In accordance with an aspect of the disclosure, a connector cover configured to be used in an ultrasonic probe connector includes a case, and a coupling device disposed at one end portion in the case and configured to be coupled to the connector. The coupling device includes a body including a fastening portion configured to be coupled to a connector protrusion provided to protrude from the connector toward a first direction, and a rotating shaft connected to the case and the body, and the connector cover is configured to be coupled to the connector along a second direction.

The rotating shaft may be rotatably coupled to the case to allow the body to be moved in the first direction.

The body may further include a guide formed in one end portion of the body coupled to the connector protrusion and inclined upward in the second direction, and the body may be rotated by the rotating shaft to allow the fastening portion to be coupled to the connector protrusion.

The coupling device may further include an elastic member provided between the case and the coupling device and configured to elastically press the body toward the connector protrusion.

The fastening portion may be a first fastening portion, the connector protrusion may be a first protrusion, the body may further include a second fastening portion, the first fastening portion and the second fastening portion may be spaced apart from each other, the first fastening portion may be configured to be coupled to the first protrusion, and the second fastening portion may be configured to be coupled to a second protrusion provided to protrude from the connector toward the first direction.

The coupling device may be a first coupling device, and the coupling device may further include a second coupling device disposed at the other end of the case and configured to be coupled to the connector.

The fastening portion may include a fastening hole and a fastening groove provided on an upper portion of the body to be coupled to the connector protrusion.

The connector cover may further include a case hole provided to pass through the case along the first direction, and a push rod configured to move the body toward the first direction through the case hole so as to separate the coupling device and the connector.

The fastening portion may be formed on the upper portion of the body, and the push rod may be configured to push a lower portion of the body with respect to the rotating shaft.

The fastening portion may include a hook configured to be coupled to the connector protrusion, and the rotating shaft may extend in the first direction and then connected to the case and the body.

In accordance with another aspect of the disclosure, a connector cover configured to be used in an ultrasonic probe connector includes a case, and a coupling device disposed at one side in the case and configured to be coupled to the connector. The coupling device includes a body including a hook configured to be coupled to a connector protrusion provided to protrude from the connector along a first direction, and a fixed shaft provided to extend in the first direction to be connected to the case and the body, and the connector cover is configured to be coupled to the connector along a second direction.

The hook may be a first hook, the connector protrusion may be a first protrusion, the body may further include a second hook, the first hook and the second hook may be spaced apart from each other, the first hook may be configured to be coupled to the first protrusion, and the second hook may be configured to be coupled to a second protrusion provided to protrude from the connector toward the first direction.

The coupling device may be a first coupling device, and the coupling device may further include a second coupling device disposed at the other end of the case and configured to be coupled to the connector.

In accordance with another aspect of the disclosure, an ultrasonic probe assembly includes an ultrasonic probe, a connector connected to the ultrasonic probe, and a connector cover configured to be used in the connector. The connector includes a connector protrusion provided to protrude from the connector along a first direction to be coupled to a medical device. The connector cover includes a case, and a coupling device disposed at one end portion in the case and configured to be coupled to the connector. The coupling device includes a body including a fastening portion configured to be coupled to the connector protrusion, and a rotating shaft connected to the case and the body, and the connector and the connector cover are coupled to each other along a second direction.

The rotating shaft may be rotatably coupled to the case to allow the body to be moved in the first direction.

The body may further include a guide formed in one end portion of the body coupled to the connector protrusion and inclined upward in the second direction, and the body may be rotated by the rotating shaft to allow the fastening portion to be coupled to the connector protrusion.

The coupling device may further include an elastic member provided between the case and the coupling device and configured to elastically press the body toward the connector protrusion.

The connector protrusion may be a first protrusion, the connector may further include a second protrusion formed to be spaced apart from the first protrusion and provided to protrude along the first direction, the fastening portion may be a first fastening portion configured to be coupled to the first protrusion, and the body may further include a second fastening portion formed to be spaced apart from the first fastening portion and configured to be coupled to the second protrusion.

The ultrasonic probe assembly may further include a case hole provided to pass through the case along the first direction, and a push rod configured to move the body toward the first direction through the case hole so as to separate the coupling device and the connector.

The fastening portion may be formed on an upper portion of the body, and the push rod may be configured to push a lower portion of the body with respect to the rotating shaft.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
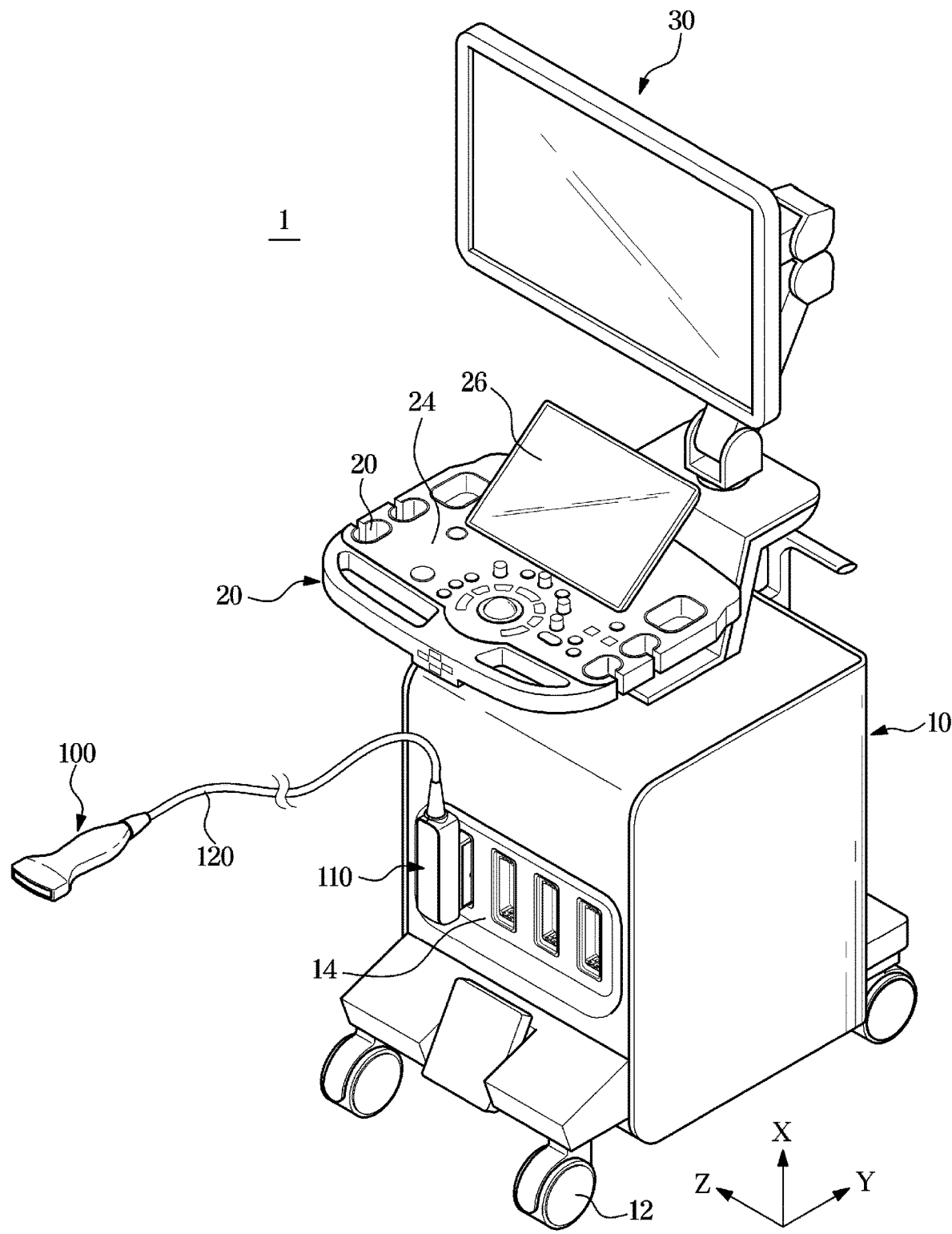
FIG. 1 is a view illustrating a medical device and an ultrasonic probe assembly according to an embodiment of the disclosure.

Embodiments described in the disclosure and configurations shown in the drawings are merely examples of the embodiments of the disclosure, and may be modified in various different ways at the time of filing of the present application to replace the embodiments and drawings of the disclosure.

In addition, the same reference numerals or signs shown in the drawings of the disclosure indicate elements or components performing substantially the same function.

Also, the terms used herein are used to describe the embodiments and are not intended to limit and/or restrict the disclosure. The singular forms "a," "an" and "the" are intended to include the plural forms as well, unless the context clearly indicates otherwise. In this disclosure, the terms "including", "having", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, but elements are not limited by these terms. These terms are only used to distinguish one element from another element. For example, without departing from the scope of the disclosure, a first element may be termed as a second element, and a second element may be termed as a first element. The term of "and/or" includes a plurality of combinations of relevant items or any one item among a plurality of relevant items.

In the following detailed description, the terms of "front side", "rear side", "left side", "right side", and the like may be defined by the drawings, but the shape and the location of the component is not limited by the term.

Figure 2:
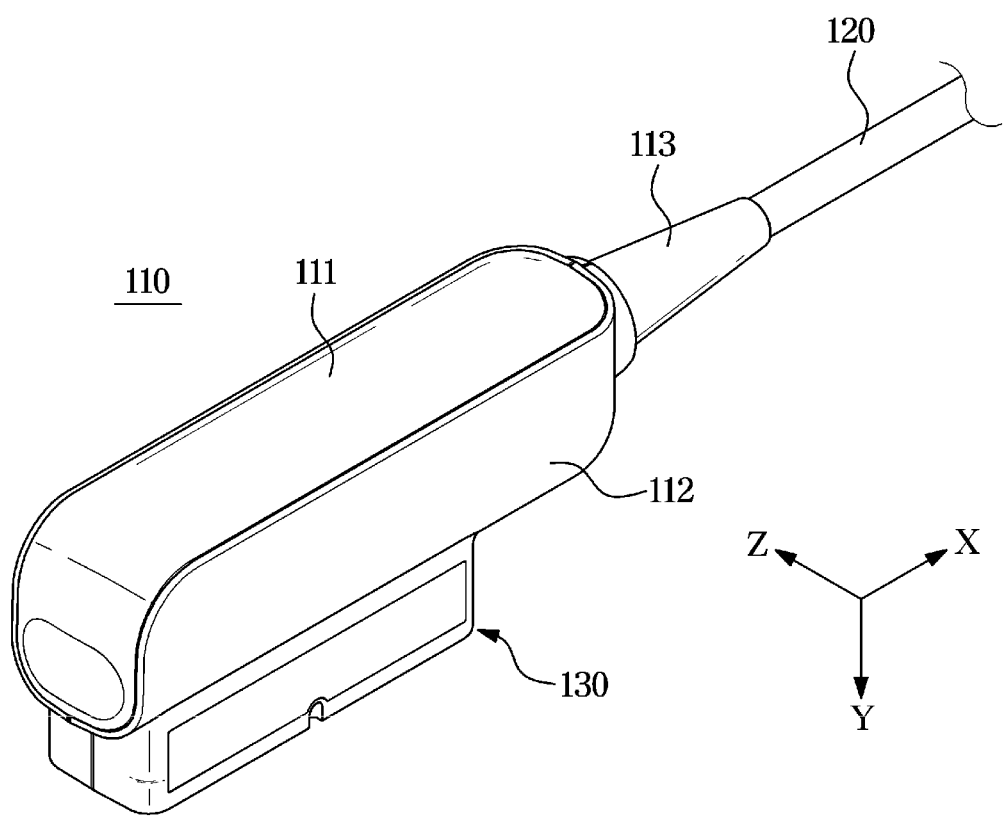
FIG. 2 is a view illustrating a connector in the ultrasonic probe assembly shown in FIG. 1.

Particularly, as shown in FIG. 2, a direction of a connector to which a cable is not connected is defined as a front side, and a direction of the connector to which the cable is connected is defined a rear side. Left and right sides and upper and lower sides are defined based on this.

The disclosure will be described more fully hereinafter with reference to the accompanying drawings FIG. 1 is a view illustrating a medical device and an ultrasonic probe assembly according to an embodiment of the disclosure.

Referring to FIG. 1, a medical device 1 according to an embodiment may include a main body 10 and an ultrasonic probe 100 configured to transmit an ultrasound signal to an object to be diagnosed and receive a signal reflected from the object. The ultrasonic probe 100 may be connected to the main body 10 by a cable 120.

The ultrasonic probe 100 may be mounted on the main body 10 by a holder 22. When the medical device 1 is not in use, an examiner may mount the ultrasonic probe 100 to the holder 22 and store the ultrasonic probe 100. FIG. 1 illustrates that the holder 22, to which the ultrasonic probe 100 is mounted, is provided on a control panel 20, but the holder 22 may be provided on the main body 10 according to the user's convenience. Alternatively, the holder 22 may be provided on both the main body 10 and the control panel 20.

A moving device 12 may be provided in the main body 10 to move the medical device 1. The moving device 12 may be a plurality of casters provided on a bottom surface of the main body 10. The casters may be configured to be aligned to move the main body 10 to a specific direction, configured to be freely movable so as be movable to any direction, and configured to be locked to be stopped at a specific location.

The ultrasonic probe 100 may include an ultrasonic transmitter and receiver provided in a housing. The ultrasonic transmitter and receiver may include a transducer module (not shown) configured to irradiate ultrasonic waves to an object, receive echo ultrasonic waves reflected from the object, and interconvert electrical signals and ultrasonic waves. The medical device 1 may include a male connector 110 configured to transmit and receive a signal to and from the main body 10 by being physically coupled to a female connector 14 of the main body 10, and the cable 120 configured to connect the male connector 110 to the transducer module (not shown). The male connector 110 may be referred to as a connector 110.

The object may be a living body of a human or an animal, or tissue in vivo such as blood vessels, bones, muscles, etc., but is not limited thereto. Therefore, the object may be an object as long as its internal structure can be imaged by the medical device 1.

The ultrasonic probe assembly may include the ultrasonic probe 100, the cable 120, the connector 110, and a connector cover 140 to be described later.

A display 30 and the control panel 20 may be provided on the main body 10 of the medical device 1. An inputter 24 configured to allow a user to control the medical device 1 may be provided on the control panel 20. The inputter 24 may receive not only setting information, but also various control commands on the ultrasonic probe 100 from a user.

An auxiliary display 26 may be provided on the control panel 20. The auxiliary display 26 may provide related information such as a menu for optimizing an ultrasound image or an auxiliary image, or may provide a graphic interface to a user.

Figure 3:
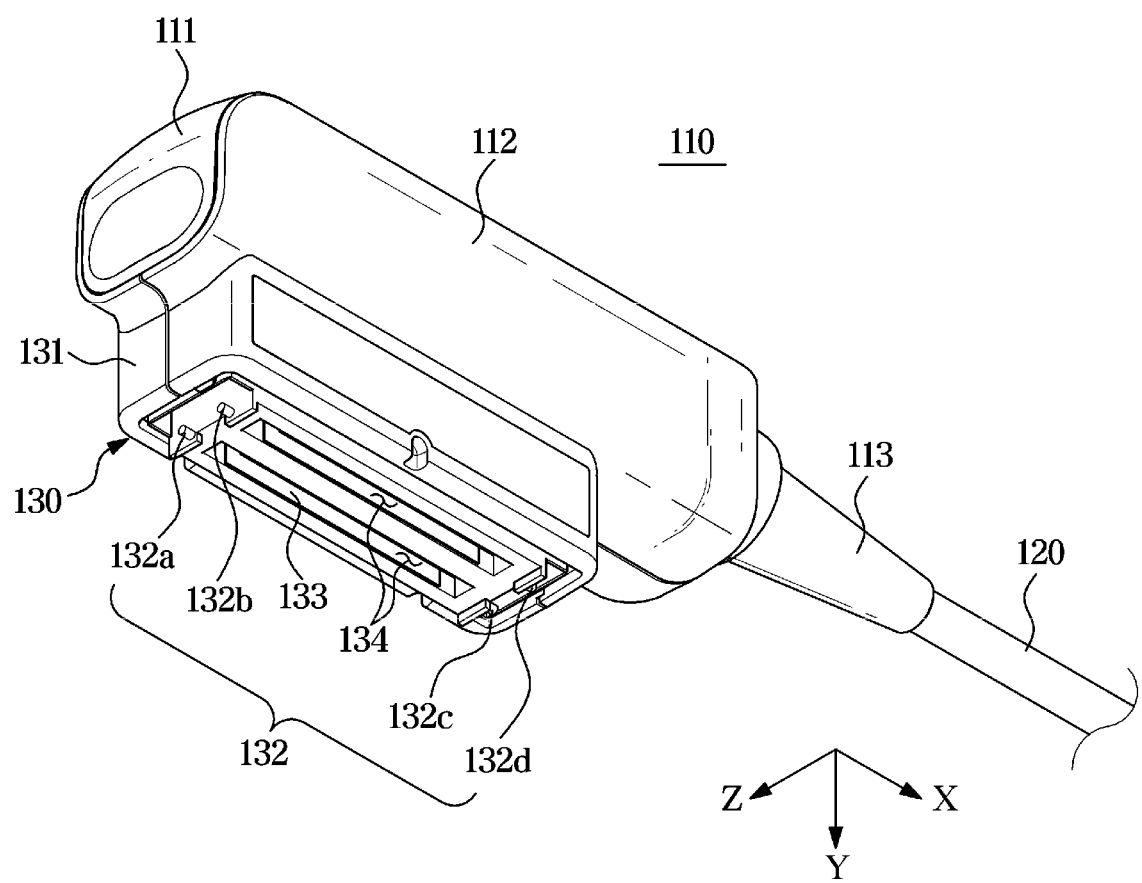
FIG. 3 is a view illustrating a bottom of the connector in the ultrasonic probe assembly shown in FIG. 1.

FIG. 2 is a view illustrating a connector in the ultrasonic probe assembly shown in FIG. 1. FIG. 3 is a view illustrating a bottom of the connector in the ultrasonic probe assembly shown in FIG. 1.

Referring to FIGS. 2 and 3, the connector 110 may include the housing and a connection device 130.

The housing may include an upper housing 111, a side housing 112, and a connection housing 113. The upper housing 111 may be positioned in an upper portion of the connector 110 to form an upper surface and a front surface of the connector 110. The side housing 112 may form a left side and a right side of the connector 110. The connection housing 113 may form an exterior of a region connected to the cable 120. Accordingly, the connection housing 113 may be connected to the cable 120. The cable 120 may receive or supply a signal from or to the connector 110 that is connected.

The connection device 130 may be provided in a lower portion of the connector 110. The connection device 130 may include a case 131, a connection terminal 132, and a circuit board 133. The case 131 may form an outer surface of the connection device 130 to form an exterior of the connection device 130.

The connection terminal 132 may protrude from an inside to an outside of the connector 110 in a first direction X. The connection terminal 132 may be referred to as a connector protrusion 132. The connector protrusion 132 may be configured to be connected to the main body of the medical device. However, it is not limited thereto, and the connector protrusion 132 may not be connected to the main body 10 of the medical device 1 but be connected to the connector cover 140 to be described later. The connector protrusion 132 may be provided in plural as shown, but is not limited thereto. Therefore, a single connector protrusion may be provided.

Because the connector cover 140 is coupled with the connector 110 through the connection terminal 132 of the connector 110 used for the medical device 1 that is the connector protrusion 132, it is possible to reduce additional manufacturing and component costs.

The connector protrusion 132 may include a first protrusion 132a, a second protrusion 132b, a third protrusion 132c, and a fourth protrusion 132d.

The first protrusion 132a and the second protrusion 132b may be provided at one end of the connection device 130 and coupled to a first coupling device 150a to be described later. The third protrusion 132c and the fourth protrusion 132d may be provided at the other end of the connection device 130 and coupled to a second coupling device 150b to be described later.

The first protrusion 132a and the second protrusion 132b may be provided adjacent to the front surface of the connector 110. The third protrusion 132c and the fourth protrusion 132d may be provided adjacent to the rear surface of the connector 110.

The circuit board 133 may be provided in the inside of the connection device 130. The circuit board 133 may be connected to the main body of the medical device to transmit signals, which are transmitted and received by the ultrasonic probe, to the medical device.

The connection terminal 132 may further include a connecting portion 134. The connecting portion 134 may be configured to be coupled to the main body 10 of the medical device 1. Accordingly, the connecting portion 134 may be formed in a shape corresponding to the main body 10.

Figure 4:
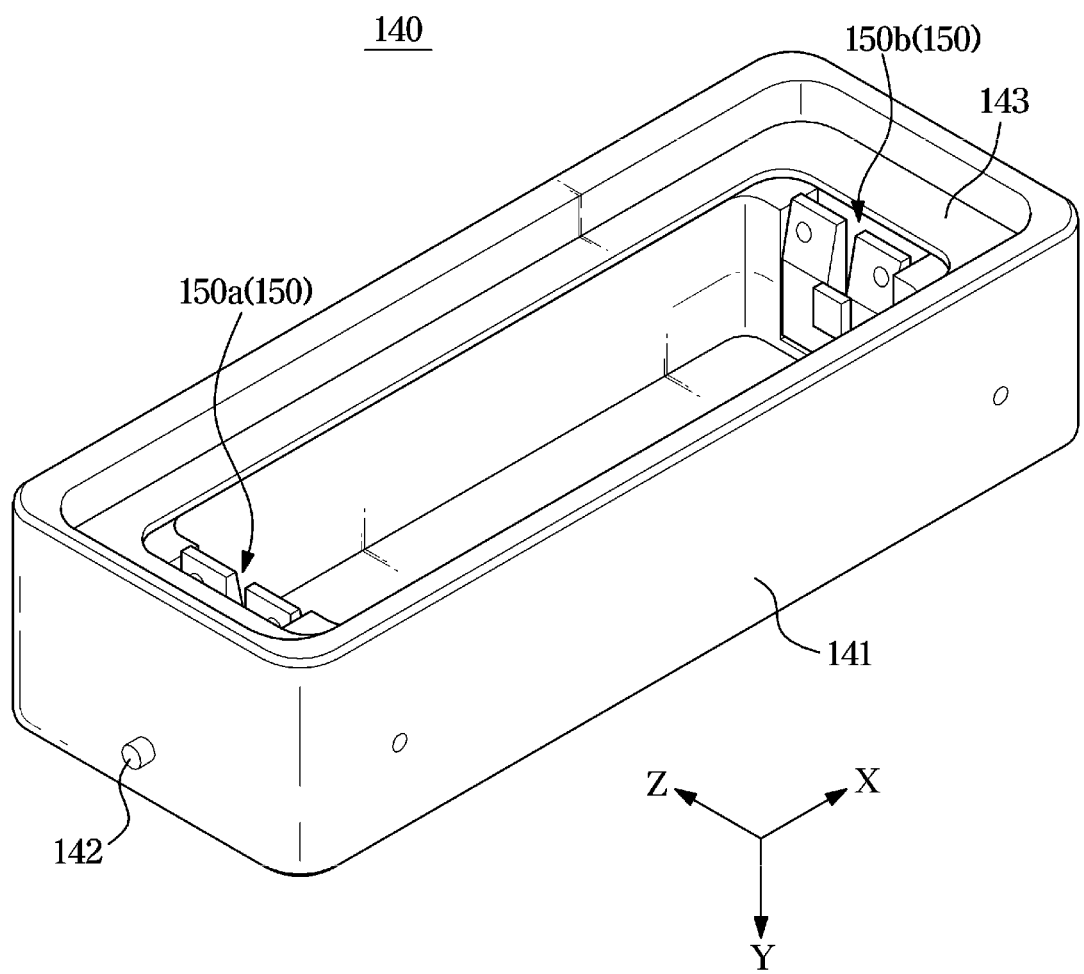
FIG. 4 is a view illustrating a connector cover in the ultrasonic probe assembly shown in FIG. 1.

FIG. 4 is a view illustrating a connector cover in the ultrasonic probe assembly shown in FIG. 1.

Referring to FIG. 4, the connector cover 140 may include a case 141, a push rod 142, a packing member 143, and a coupling device 150.

The case 141 may be formed on the outside of the connector cover 140 to surround a portion coupled to the connector 110. The case 141 may be formed in a rectangular parallelepiped shape. However, it is not limited thereto and may be formed in various shapes such as a regular tetrahedron.

The packing member 143 may seal a space between the connector 110 and the connector cover 140 in response to coupling between the connector 110 and the connector cover 140. The packing member 143 may be formed of silicon. However, it is not limited thereto, and thus the packing member 143 may be formed of various materials capable of sealing a coupling space between the connector 110 and the connector cover 140. The packing member 143 may be provided in a shape corresponding to the coupling region between the connector 110 and the connector cover 140.

The coupling device 150 may include the first coupling device 150a and the second coupling device 150b.

The first coupling device 150a may be arranged at one end in the case 141 and coupled to the connector 110. That is, at one end in the case 141, the first coupling device 150a may be coupled to the first protrusion 132a and the second protrusion 132b of the connector connection device 130. One end of the case 141 may be a front portion of the case 141.

The second coupling device 150b may be disposed at the other end in the case 141 and coupled to the connector 110. That is, at the other end in the case 141, the second coupling device 150*b* may be coupled to the third protrusion 132*c* and the fourth protrusion 132*d* of the connector connection device 130. The other end of the case 141 may be a rear portion of the case 141.

However, it is not limited thereto, and the first protrusion 132*a* and the second protrusion 132*b* may be coupled to the second coupling device 150*b*. The third protrusion 132*c* and the fourth protrusion 132*d* may be coupled to the first coupling device 150*a*.

Because at least one coupling device 150 is included, the connector 110 and the connector cover 140 may be firmly coupled to each other.

Figure 5A:
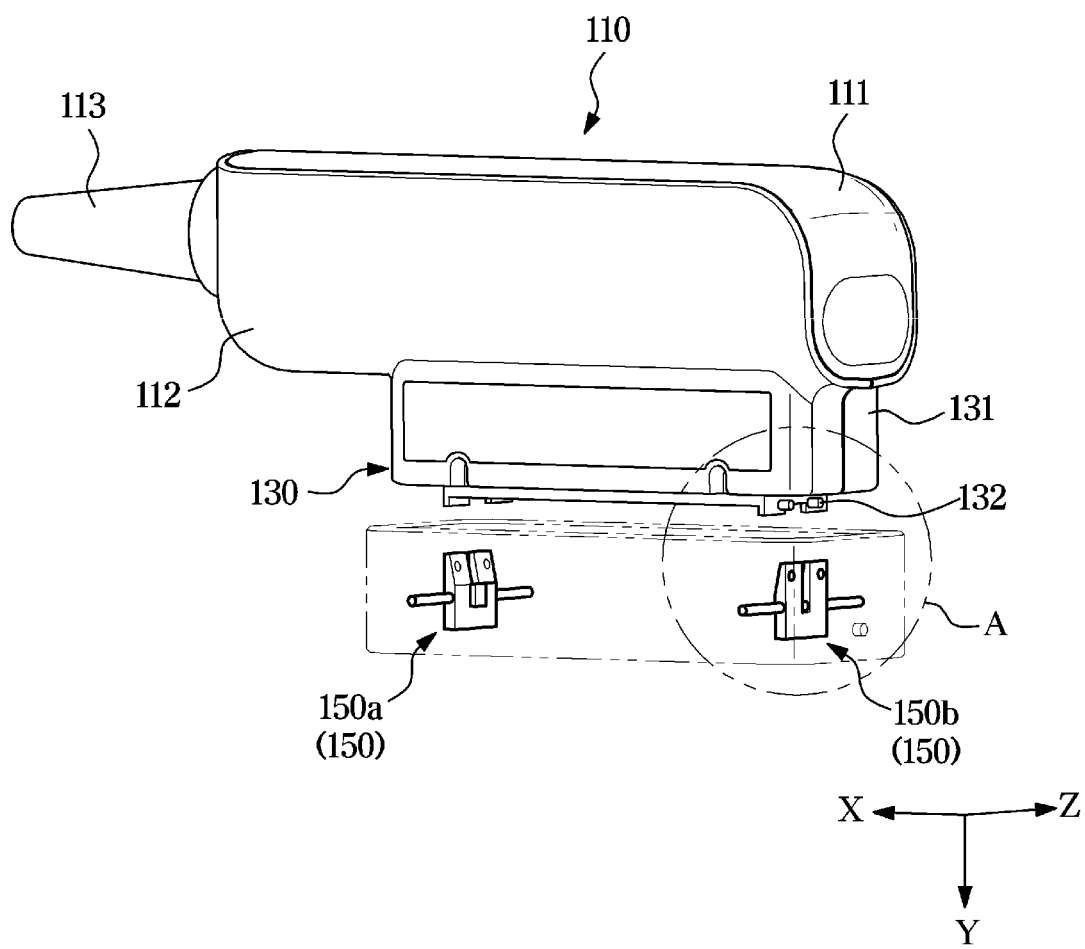
FIG. 5A is a view illustrating the connector and the connector cover in the ultrasonic probe assembly shown in FIG. 1.
Figure 5B:
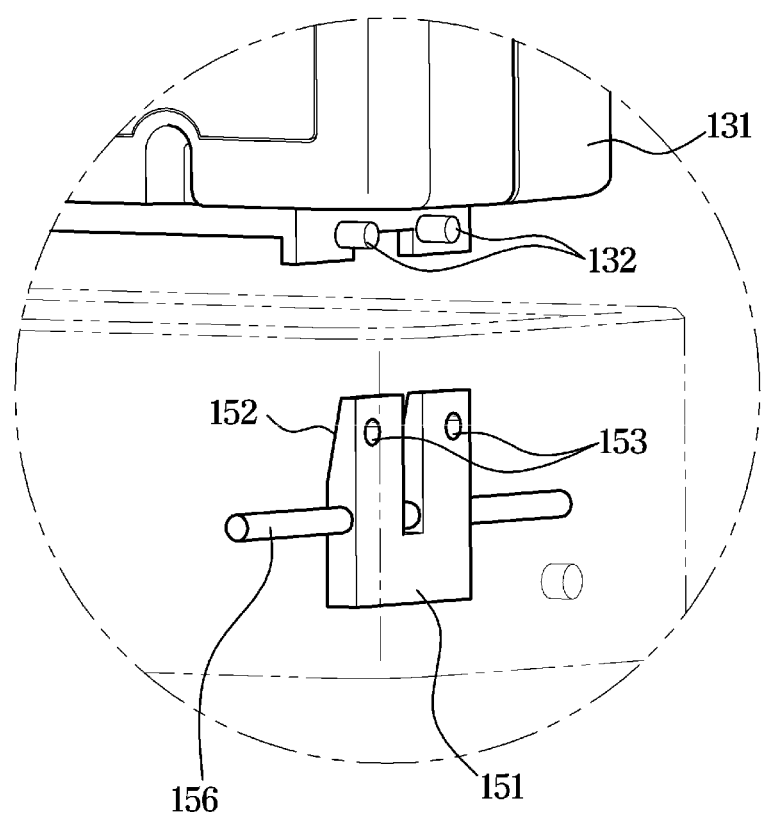
FIG. 5B is an enlarged view of A portion in the connector and the connector cover shown in FIG. 5A.

FIG. 5A is a view illustrating the connector and the connector cover in the ultrasonic probe assembly shown in FIG. 1. FIG. 5B is an enlarged view of A portion in the connector and the connector cover shown in FIG. 5A.

A description will be made based on the second coupling device 150*b*. Referring to FIGS. 5A and 5B, the connector 110 and the connector cover 140 may be coupled along a second direction Y.

The coupling device 150 may be disposed in the case 141. The coupling device 150 may include a body 151, a guide 152, and a fastening portion 153.

The body 151 may include the fastening portion 153 coupled the connector protrusion 132 protruding from the connector 110 in the first direction X. The fastening portion 153 may be formed at one end of the body 151. That is, the fastening portion 153 may be formed on the upper portion of the body 151. The fastening portion 153 may be formed in a shape corresponding to the connector protrusion 132. Accordingly, the fastening portion 153 may be formed in a cylindrical shape in accordance with the connector protrusion 132. However, it is not limited thereto, and the fastening portion 153 may be formed in various shapes as long as capable of being coupled to the connector protrusion 132. The connector 110 may be properly coupled to the connector cover 140 through the fastening portion 153.

The body 151 may be provided in a form in which a center of an upper portion is hollow. This is to make a weight of a lower portion heavier than the upper portion. That is, it is to secure a sense of stability by placing the center of gravity at the bottom. However, it is not limited thereto and the body 151 may be provided in a form in which a middle of the upper portion is filled.

In addition, the fastening portions 153 may be provided in a number corresponding to the connector protrusion 132. Accordingly, the fastening portion 153 may be formed in plural corresponding to the connector protrusion 132. However, it is not limited thereto, and a single fastening portion 153 may be provided as long as capable of being coupled to the connector protrusion 132.

The body 151 may further include the guide 152. The guide 152 may be provided in an upper portion of the body 151, which is coupled to the connector protrusion 132, and inclined upwardly toward the case 141 along the second direction Y. That is, the guide 152 may include a slope in a region adjacent to the fastening portion 153.

In response to coupling between the connector 110 and the connector cover 140 in the second direction Y, a rotating shaft 156 may be easily rotated by the guide 152, and in response to rotation of the body 151, the body 151 may be coupled to the connector protrusion 132. Therefore, by the guide 152, it is possible to easily couple the connector protrusion 132 to the body 151 without using a material having high elasticity.

The coupling device 150 may further include the rotating shaft 156. The rotating shaft 156 may be connected to the case 141 and the body 151, respectively. The rotating shaft 156 may be rotatably coupled to the case 141 to allow the body 151 to be moved along the first direction X. That is, as the connector 110 is coupled to the connector cover 140 in the second direction Y, the connector protrusion 132 moves the body 151 in the first direction X toward the case 141, and thus the body 151 may be rotated by the rotating shaft 156. The body 151 may be moved from the connector protrusion 132 to the case 141 of the connector cover 140.

Because the body is rotated due to the rotating shaft and then coupled to the connector protrusion, the connector protrusion and the body may be easily coupled to each other without using a material having high elasticity.

The rotating shaft 156 may be a fixed shaft extending in the first direction X in relation to a hook to be described later.

The rotating shaft 156 may be provided in the first coupling device 150*a* and the second coupling device 150*b*, respectively. Accordingly, both the first coupling device 150*a* and the second coupling device 150*b* may be rotated. That is, as for the first coupling device 150*a* and the second coupling device 150*b*, the body 151 may be moved from the connector protrusion 132 to the case 141 of the connector cover 140, respectively.

Figure 6A:
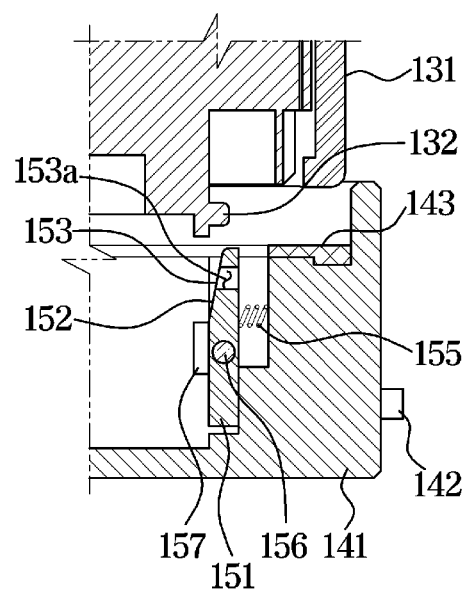
FIGS. 6A-6C are views illustrating a coupling process of the connector and the connector cover shown in FIG. 5A.
Figure 6B:
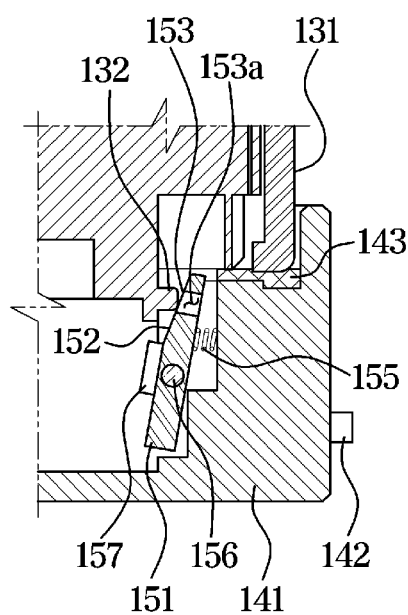
Figure 6C:
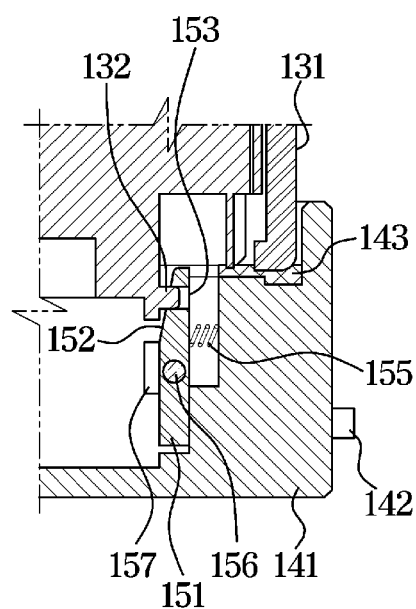

FIGS. 6A-6C are views illustrating a coupling process of the connector and the connector cover shown in FIG. 5A.

Referring to FIGS. 6A-6C, the fastening portion 153 may include a fastening hole 153*a*. The fastening hole 153*a* may pass through an upper portion of the body 151 along the first direction X. That is, the fastening hole 153 may allow the connector protrusion 132 to be coupled to the fastening portion 153. A shape of the fastening hole 153*a* may extend in a cylindrical shape in accordance with the shape of the connector protrusion 132. However, it is not limited thereto, and the fastening hole 153*a* may include various shapes configured to be coupled to the connector protrusion 132.

The connector cover 140 may further include an elastic member 155.

The elastic member 155 may be provided between the case 141 and the coupling device 150 to elastically press the body 151 toward the connector protrusion 132. That is, in response to coupling, the connector protrusion 132 may press the coupling device 150 in the first direction X and the elastic member 155 may press the body 151 to a direction opposite to a direction in which the connector protrusion 132 presses, by the elastic force of the elastic member 155. Accordingly, after the connector 110 and the connector cover 140 are coupled to each other, the body 151 may return to a position that is before the coupling begins. The elastic member 155 may include a spring. Due to the elastic member 155, the body 151 may return to its original position that is before and after rotation.

The elastic member 155 may be provided between the first coupling device 150*a* and the case 141 to press the first coupling device 150*a*. In addition, the elastic member 155 may be provided between the second coupling device 150*b* and the case 141 to press the second coupling device 150*b*. That is, one or more elastic members 155 may be provided.

The drawing illustrates that the elastic member 155 pushes the upper portion of the body 151, but is not limited thereto. Therefore, the elastic member 155 may be arranged at a different location as long as allowing the body 151 to expand in the second direction Y after the completion of the coupling and separation.

The connector cover 140 may further include the push rod 142. This will be described later.

The coupling device 150 may further include a frame member 157.

The frame member 157 is formed smaller than the body 151 and may be attached to the body 151. The frame member 157 may be disposed closer to the inside of the case 141 than the body 151. The frame member 157 may add a weight in the opposite direction of rotation in response to the coupling, thereby allowing the body 151 to return to an initial state after being rotated in the first direction X. The frame member 157 may be provided in the first coupling device 150a and the second coupling device 150b, respectively. The frame member 157 may be integrally formed with the body 151. However, it is not limited thereto and the frame member 157 and the body 151 may be separately formed and coupled to each other.

A coupling process will be described.

As shown in FIG. 6A, in response to movement of one or each of the connector 110 and the connector cover 140 toward the second direction Y, the coupling starts. At this time, the connector protrusion 132 is adjacent to the guide 152 of the coupling device 150.

As shown in FIG. 6B, in response to contact between the connector protrusion 132 and the guide 152, the body 151 may be moved in the first direction X by the rotating shaft 156. In response to the movement of the body 151 in the first direction X, the elastic member 155 is compressed. The elastic member 155 may be compressed until the connector protrusion 132 is coupled to the fastening portion 153.

As shown in FIG. 6C, in response to the completion of the coupling between the connector protrusion 132 and the fastening portion 153, the elastic member 155 may press the body 151 toward the inside of the case 141, and due to the weight of the frame member 157, the body 151 may be disposed at the same position as before the coupling. At this time, the case 141 of the connector 110 is in contact with the packing member 143 of the connector cover 140 to prevent a liquid from entering.

Figure 7A:
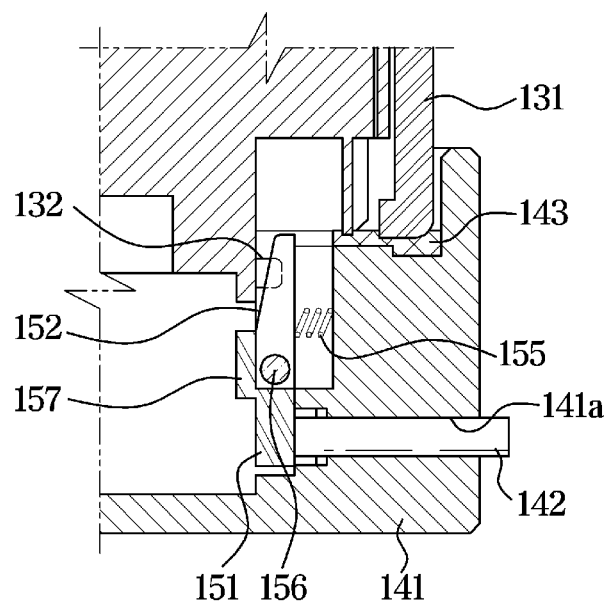
FIGS. 7A and 7B are views illustrating a separation process of the connector and the connector cover shown in FIG. 5A.
Figure 7A:
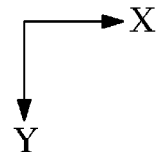
Figure 7B:
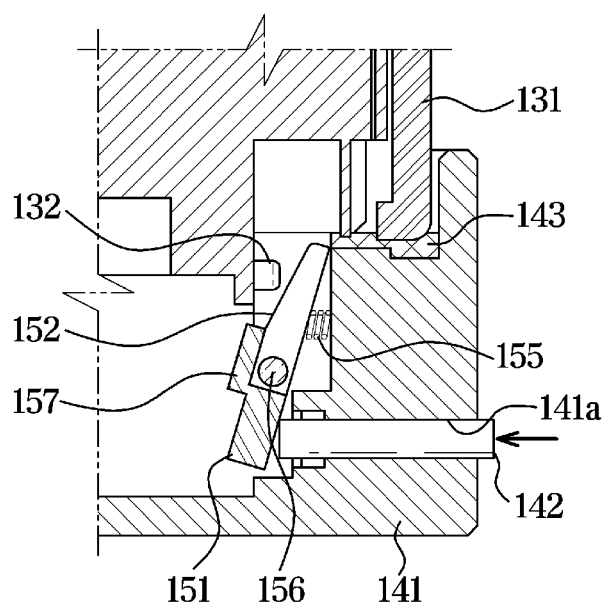

FIGS. 7A and 7B are views illustrating a separation process of the connector and the connector cover shown in FIG. 5A.

Referring to FIG. 7A, the connector cover 140 may further include a case hole 141a and the push rod 142.

The case hole 141a may be formed in a lower portion of the case 141 along the first direction X. The case hole 141a may be provided to allow the push rod 142 to push the body 151 of the coupling device 150 and thus the case hole 141a may be provided at one end or other end of the case 141. That is, more than one case hole 141a may be provided in accordance with the number of coupling devices 150.

The case hole 141a may be formed in a cylindrical shape. However, it is not limited thereto, and the case hole 141a may be formed in various shapes as long as corresponding to the shape of the push rod 142.

The push rod 142 may be provided to move the body 151 in the first direction X through the case hole 141a to separate the coupling device 150 from the connector 110. The push rod 142 may push the lower portion of the body 151 to separate the fastening portion 153 from the connector protrusion 132.

The push rod 142 may be formed in a cylindrical shape, but is not limited thereto. Therefore, the push rod 142 may include various shapes as long as corresponding to the shape of the case hole 141a. Because the push rod 142 is provided in accordance with the number of the case holes 141a, and thus more than one push rod 142 may be provided.

The connector 110 and the connector cover 140 may be easily separated through the case hole 141a and the push rod 142.

A separation process will be described.

A user can push the push rod 142 toward the body 151 of the coupling device 150 in the first direction X. The push rod 142 may push a position opposite to the position of the fastening portion 153 of the body 151. That is, the push rod 142 may push the lower portion corresponding to the other end of the body 151. By pushing the push rod 142, the body 151 may be rotated by the rotating shaft 156 along the first direction X, and the connector protrusion 132 and the fastening portion 153 may be separated.

Referring to FIG. 7B, in response to pushing the body 151 by the push rod 142 to separate the connector 110 and the connector cover 140, the elastic member 155 is compressed. In response to the completion of the separation of the connector protrusion 132 and the coupling device 150, a user can make each component apart from each other toward the second direction Y, thereby completely separating each component. After the separation, the body 151 of the coupling device 150 may return to the same position as the position at the time of coupling by the elastic force of the elastic member 155.

Figure 8A:
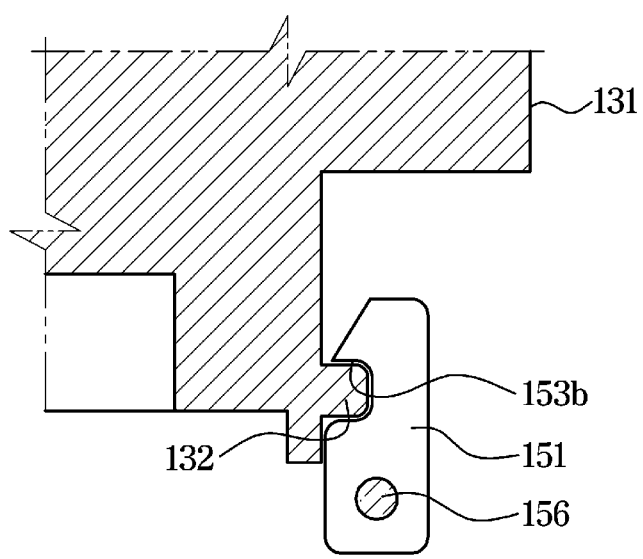
FIGS. 8A and 8B are views illustrating a coupling device in an ultrasonic probe assembly according to another embodiment of the disclosure.
Figure 8B:
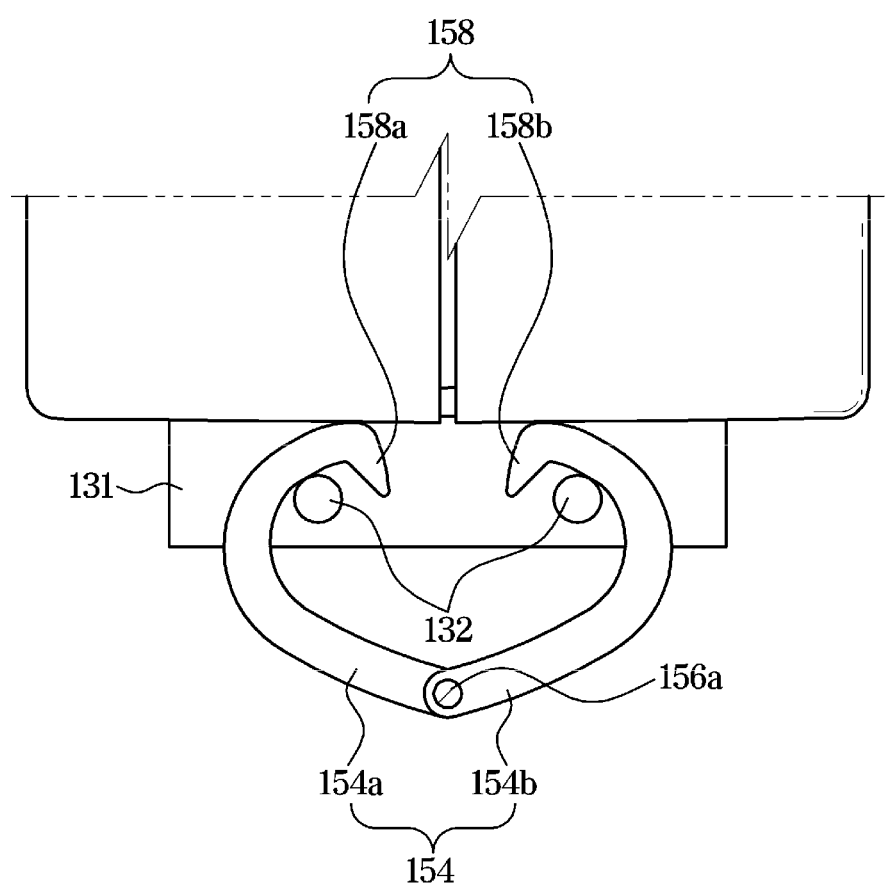

FIGS. 8A and 8B are views illustrating a coupling device in an ultrasonic probe assembly according to another embodiment of the disclosure.

The description of the basic configuration of the coupling device 150 has been described above with reference to FIGS. 4 to 7, and thus the same description will be omitted and only different components will be described.

Referring to FIG. 8A, a body 151 of a coupling device 150 may further include a fastening groove 153b.

The fastening groove 153b may be formed in an upper portion of the body 151 along a first direction X. That is, the fastening groove 153b may allow a connector protrusion 132 to be coupled to a fastening portion 153. A shape of the fastening groove 153b may extend in a cylindrical shape in accordance with the shape of the connector protrusion 132. However, it is not limited thereto, and the fastening groove 153b may include various shapes configured to be coupled to the connector protrusion 132.

Referring to FIG. 8B, the coupling device 150 may further include a hook 154 coupled to the connector protrusion 132 and a fixed shaft 156a.

The hook 154 may include hook portions 158a and 158b formed at one end of the hook 154 and configured to prevent the hook 154 from being separated from the connector protrusion 132. At one end of the hook 154, the hook portions 158a and 158b may be fastened with the connector protrusion 132. The other end of the hook 154 may be rotatably coupled to the fixed shaft 156a.

The fixed shaft 156a may extend in the first direction X and coupled to the case 141 of the connector cover 140.

More than one hook 154 may be provided to be coupled to the connector protrusion 132 provided in plurality. The hook 154 may include a first hook 154a and a second hook 154b. The first hook 154a may be coupled to a first protrusion 132a, and the second hook 154b may be coupled to a second protrusion 132b.

The first hook 154a may include the first hook portion 158a, and the second hook 154b may include the second hook portion 158b.

Due to the hook 154, the connector protrusion 132 and the coupling device 150 may be firmly coupled to each other. That is, the connector 110 and the connector cover 140 may be coupled to each other.

The drawing illustrates two hooks 154, but is not limited thereto. Therefore, one or more than three hooks may be provided as long as capable of firmly being coupled to the connector protrusion 132.

As is apparent from the above description, it is possible to provide a connector cover and an ultrasonic probe assembly with reduced cost because the conventional connector connection terminal is used.

It is possible to provide an ultrasonic probe assembly with improved reliability by preventing corrosion and damage by using the connector cover.

It is possible to provide a connector cover configured to be easily coupled to an ultrasonic probe connector by using a coupling device.

Although a few embodiments of the disclosure have been shown and described, it would be appreciated by those skilled in the art that changes may be made in these embodiments without departing from the principles and spirit of the disclosure, the scope of which is defined in the claims and their equivalents.

What is claimed is:

1. A connector cover configured to be used in an ultrasonic probe connector comprising:
a case; and
a coupling device disposed at one end portion in the case and configured to be coupled to the connector,
wherein the coupling device comprises
a body comprising a fastening portion configured to be coupled to a connector protrusion provided to protrude from the connector toward a first direction; and
a rotating shaft connected to the case and the body,
wherein the connector cover is configured to be coupled to the connector along a second direction, and
wherein the fastening portion comprises a fastening hole or a fastening groove provided on an upper portion of the body to be coupled to the connector protrusion.

2. The connector cover of claim 1, wherein
the rotating shaft is rotatably coupled to the case to allow the body to be moved in the first direction.

3. The connector cover of claim 2, wherein
the body further comprises a guide formed in one end portion of the body coupled to the connector protrusion and inclined upward in the second direction,
wherein the body is rotated by the rotating shaft to allow the fastening portion to be coupled to the connector protrusion.

4. The connector cover of claim 3, wherein
the coupling device further comprises an elastic member provided between the case and the coupling device and configured to elastically press the body toward the connector protrusion.

5. The connector cover of claim 1, wherein
the fastening portion is a first fastening portion, the connector protrusion is a first protrusion, and the body further comprises a second fastening portion,
wherein the first fastening portion and the second fastening portion are spaced apart from each other,
wherein the first fastening portion is configured to be coupled to the first protrusion, and the second fastening portion is configured to be coupled to a second protrusion provided to protrude from the connector toward the first direction.

6. The connector cover of claim 1, wherein
the coupling device is a first coupling device, and
the coupling device further comprises a second coupling device disposed at the other end of the case and configured to be coupled to the connector.

7. The connector cover of claim 2, further comprising:
a case hole provided to pass through the case along the first direction; and
a push rod configured to move the body toward the first direction through the case hole so as to separate the coupling device and the connector.

8. The connector cover of claim 7, wherein
the fastening portion is formed on the upper portion of the body, and
the push rod is configured to push a lower portion of the body with respect to the rotating shaft.

9. The connector cover of claim 1, wherein:
the fastening portion comprises a hook configured to be coupled to the connector protrusion, and the rotating shaft extends in the first direction and then connected to the case and the body.

10. A connector cover configured to be used in an ultrasonic probe connector comprising:
a case; and
a coupling device disposed at one side in the case and configured to be coupled to the connector,
wherein the coupling device comprises
a body comprising a hook configured to be coupled to a connector protrusion provided to protrude from the connector along a first direction; and
a fixed shaft provided to extend in the first direction to be connected to the case and the body,
wherein the connector cover is configured to be coupled to the connector along a second direction, and
wherein the coupling device is disposed in an inner space of the case where the connector is inserted.

11. The connector cover of claim 10, wherein
the hook is a first hook, the connector protrusion is a first protrusion, and the body further comprises a second hook,
wherein the first hook and the second hook are spaced apart from each other,
wherein the first hook is configured to be coupled to the first protrusion, and the second hook is configured to be coupled to a second protrusion provided to protrude from the connector toward the first direction.

12. The connector cover of claim 11, wherein
the coupling device is a first coupling device, and
the coupling device further comprises a second coupling device disposed at the other end of the case and configured to be coupled to the connector.

13. An ultrasonic probe assembly comprising:
an ultrasonic probe;
a connector connected to the ultrasonic probe; and
a connector cover configured to be used in the connector,
wherein the connector comprises a connector protrusion provided to protrude from the connector along a first direction to be coupled to a medical device,
wherein the connector cover comprises
a case; and
a coupling device disposed at one end portion in the case and configured to be coupled to the connector,
wherein the coupling device comprises
a body comprising a fastening portion configured to be coupled to the connector protrusion; and
a rotating shaft connected to the case and the body,
wherein the connector and the connector cover are coupled to each other along a second direction.

14. The ultrasonic probe assembly of claim 13, wherein
the rotating shaft is rotatably coupled to the case to allow the body to be moved in the first direction.

15. The ultrasonic probe assembly of claim 14, wherein the body further comprises a guide formed in one end portion of the body coupled to the connector protrusion and inclined upward in the second direction,
wherein the body is rotated by the rotating shaft to allow the fastening portion to be coupled to the connector protrusion.

16. The ultrasonic probe assembly of claim 15, wherein the coupling device further comprises an elastic member provided between the case and the coupling device and configured to elastically press the body toward the connector protrusion.

17. The ultrasonic probe assembly of claim 13, wherein the connector protrusion is a first protrusion, and the connector further comprises a second protrusion formed to be spaced apart from the first protrusion and provided to protrude along the first direction,
wherein the fastening portion is a first fastening portion configured to be coupled to the first protrusion, and the body further comprises a second fastening portion formed to be spaced apart from the first fastening portion and configured to be coupled to the second protrusion.

18. The ultrasonic probe assembly of claim 14, further comprising:
a case hole provided to pass through the case along the first direction; and
a push rod configured to move the body toward the first direction through the case hole so as to separate the coupling device and the connector.

19. The ultrasonic probe assembly of claim 18, wherein the fastening portion is formed on an upper portion of the body, and
the push rod is configured to push a lower portion of the body with respect to the rotating shaft.

* * * * *